US005572568A

United States Patent [19]
Kanemitsu

[11] Patent Number: 5,572,568
[45] Date of Patent: Nov. 5, 1996

[54] X-RAY DIAGNOSTIC TABLE CAPABLE OF DISPLAYING A CENTER OF AN X-RAY VISUAL FIELD

[75] Inventor: Shingo Kanemitsu, Tochigiken, Japan

[73] Assignee: Kabushiki Kaisha Toshiba, Kawasaki, Japan

[21] Appl. No.: 473,943

[22] Filed: Jun. 7, 1995

[30] Foreign Application Priority Data

Jun. 15, 1994 [JP] Japan .................................. 6-132353

[51] Int. Cl.⁶ ..................................................... A61B 6/08
[52] U.S. Cl. .......................... 378/206; 378/205; 378/190
[58] Field of Search .................................. 378/204, 205, 378/206, 189, 190, 193, 195, 172, 173

[56] References Cited

U.S. PATENT DOCUMENTS

| 4,426,726 | 1/1984 | Cheetham | 378/206 |
| 4,836,671 | 6/1989 | Bautista | 378/208 |
| 5,283,808 | 2/1994 | Cramer et al. | 378/205 |

FOREIGN PATENT DOCUMENTS 1021814  2/1953  France ................................. 378/206

*Primary Examiner*—Don Wong
*Attorney, Agent, or Firm*—Oblon, Spivak, McClelland, Maier & Neustadt, P.C.

[57] ABSTRACT

The present invention provides a radiation diagnosis apparatus which comprises a radiation generating apparatus for emitting radiation to a subject placed on a bed, an image pickup apparatus arranged so as to face the radiation generating apparatus for picking up the radiation passed through the subject as radiation image, a first light projecting device for irradiating first light along a central axis of irradiation visual field of the radiation, and a second light projecting device for irradiating second light intersected with the first light irradiated by the first light projecting means along the central axis, whereby the center of the irradiation visual field can be indicated.

5 Claims, 3 Drawing Sheets

X-RAY DIAGNOSTIC TABLE CAPABLE OF DISPLAYING A CENTER OF AN X-RAY VISUAL FIELD

BACKGROUND OF THE INVENTION

1. Field of the Invention

The present invention relates to a radiation diagnosis apparatus capable of indicating a center of radiation visual field.

2. Description of the Prior Art

Conventionally, there has been a radiation diagnosis apparatus wherein radiation (radiant ray) is irradiated to a subject (a person to be diagnosed) placed on a bed, and then the radiation passed through the subject is converted into an electric signal by an I.I (image intensifier) etc. to be displayed on a display apparatus. As such radiation diagnosis apparatus, an over table tube type (referred to as "over type" hereinafter) radiation diagnosis apparatus in which the radiation is irradiated to the subject from the upper side of the subject, and an under table tube type (referred to as "under type" hereinafter) radiation diagnosis apparatus in which the radiation is irradiated to the subject from the lower side of the subject have been well known in the art.

The over type radiation diagnosis apparatus has no intervening body between a field stop apparatus and the subject, whereas the under type radiation diagnosis apparatus has an intervening body such as a top plate of a housing between the field stop apparatus and the subject because of its structure. When the subject is diagnosed actually, either the over type radiation diagnosis apparatus or under type radiation diagnosis apparatus can be selected according to the contents of required diagnosis.

However, in the over type radiation diagnosis apparatus, an irradiation displaying apparatus for indicating a center of an irradiation visual field is attached to the field stop apparatus. Thus, the operator of the diagnosis apparatus can recognize the center of the irradiation visual field indicated by the irradiation displaying apparatus when the radiation is irradiated to the subject. On the other hand, since, in the under type radiation diagnosis apparatus, there exists the intervening body between the field stop apparatus and the subject, the center of the irradiation visual field could not be indicated in the same manner as in the over type radiation diagnosis apparatus.

Therefore, in case an arm of a child as the subject must be diagnosed by the under type radiation diagnosis apparatus, for instance, there have been caused some drawbacks such that the irradiation of the radiation is effected under the condition wherein the arm of the subject is not placed within the irradiation visual field.

SUMMARY OF THE INVENTION

The present invention has been made in view of the above circumstances, and it is an object of the present invention to provide a radiation diagnosis apparatus capable of indicating a center location of radiation visual field even if, as in an under type radiation diagnosis apparatus etc., there exists an intervening body between a field stop apparatus and a subject.

In order to attain the above object, according to the present invention, there is provided a radiation diagnosis apparatus comprising a radiation generating means for emitting radiation to a subject placed on a bed, an image pickup means arranged so as to face the radiation generating means, for picking up the radiation passed through the subject as radiation image, a first light projecting means for irradiating first light along a central axis of irradiation visual field of the radiation, and a second light projecting means for irradiating second light intersected with the first light irradiated by the first light projecting means along the central axis.

In addition, the first and second light projecting means are displaced on the outside of the irradiation visual field of said radiation. Therefore, the radiation visual field is never blocked.

DESCRIPTION OF THE PREFERRED EMBODIMENTS

There will now be described preferred embodiments of the present invention hereinafter with reference to the accompanying drawings.

First, as a first embodiment of the present invention, an under type fluoroscopic photographing table capable of taking a photograph of a radiation as a spot shot will be explained.

Figure 1:
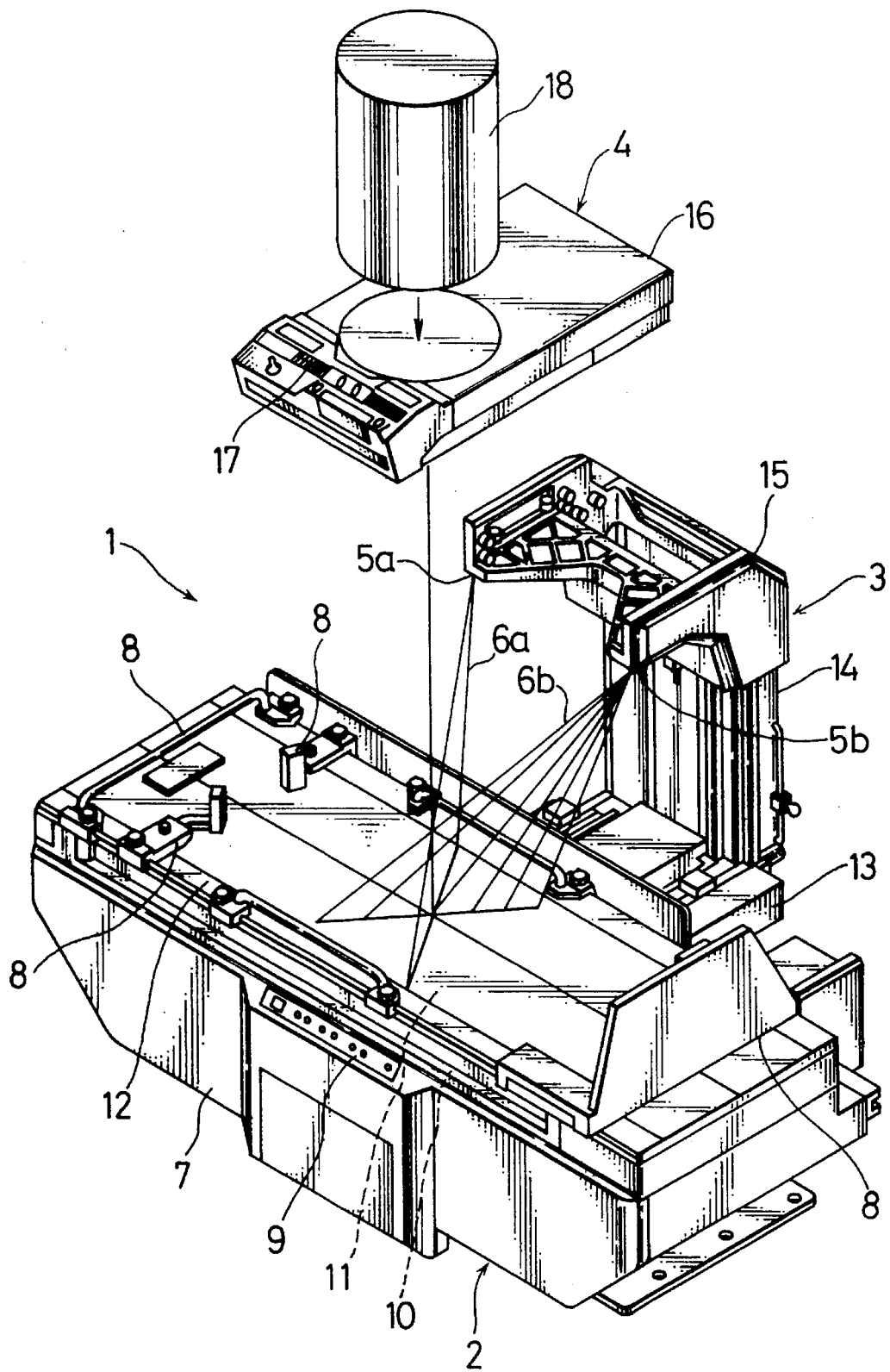
FIG. 1 is a perspective view showing a structure of a fluoroscopic photographing table according to an embodiment of a radiation diagnosis apparatus of the present invention.

FIG. 1 is an exploded perspective view showing a structure of the fluoroscopic photographing table according to the first embodiment of the present invention.

The fluoroscopic photographing table shown in FIG. 1 comprises a bed apparatus 2 which is formed in a rectangular shape as a whole and fixed to a floor plate etc. of a diagnosis room, an substantially U-shaped spot carriage apparatus 3 which is attached to a side face of the bed apparatus 2 movably in the longitudinal direction thereof and the direction (lateral direction) intersecting orthogonally to the longitudinal direction, a spot shot photographing apparatus 4 which is placed over the spot carriage apparatus 3, and a pair of light projectors 5a, 5b which are provided at upper top portions of the spot carriage apparatus 3 and emit plane light 6 to indicate a center of an X-ray irradiation visual field. First, the subject is placed on the bed apparatus 2 and then the location of the spot carriage apparatus 3 is adjusted so that an intersecting point of the light 6 emitted from the light projectors 5a, 5b should be positioned on a center of a diagnosed part of the subject. Thereafter, an X-ray is irradiated to the subject from the inside of the bed apparatus 2. The X-ray passed through the subject is converted into an electric signal by the spot shot photographing apparatus 4 which is displaced over the spot carriage apparatus 3, and the electric signal is then output from the apparatus 4.

In this case, the bed apparatus 2 comprises a rectangular bed housing 7 fixed to the floor plate, fixing devices 8 arranged on an upper surface of the bed housing 7, an operation panel 9 arranged on the front of the bed housing 7 to be operated by a doctor or an expert, an X-ray tube 10 arranged within the bed housing 7 and moved in the longitudinal direction of the bed housing 7 and the direction intersecting orthogonally to the longitudinal direction along with movements of the spot carriage apparatus 3, a field stop apparatus 11, and the like.

The spot carriage apparatus 3 comprises a long-plate like spot carriage bottom plate 13 which is attached to the side face of the bed housing 7 of the bed apparatus 2 movably in the longitudinal direction of a top plate 12 of the bed apparatus 2, an L-shaped spot carriage side plate 14 which is arranged on the spot carriage bottom plate 13 movably in the lateral direction of the top plate 12, and a spot carriage top plate 15 which is arranged on the top portion of the spot carriage side plate 14 movably in an up and down direction against the top plate 12. The X-ray tube 10, the field stop apparatus 11 etc. are fixed to the tip portion of the spot carriage side plate 14. The spot shot photographing apparatus 4 is displaced on the top portion of the spot carriage top plate 15. Upon diagnosing the subject, the doctor, the expert or the like moves the spot carriage bottom plate 13 and the spot carriage side plate 14 in the longitudinal direction and the lateral direction of the top plate 12 of the bed apparatus 2 and moves the spot carriage top plate 15 in an up and down direction against the top plate 12, so that locations of the X-ray tube 10, the field stop apparatus 11 and the spot shot photographing apparatus 4 may be adjusted.

The spot shot photographing apparatus 4 comprises a spot shot housing 16 fixed to the spot carriage top plate 15 constituting part of the spot carriage apparatus 3, an operation panel 17 provided on the front of the spot shot housing 16 to be operated by the doctor, the expert or the like, a column-shaped I.I (image Intensifier) 18 fixed to the top portion of the spot shot housing 16, and the like.

At the time of diagnosing the subject, first the location of the spot carriage apparatus 3 is adjusted and fixed. Then, the operation panel 17 is operated by the doctor etc. to output instruction on X-ray irradiation. The X-ray is emitted from the X-ray tube 10 based on this instruction. The X-ray emitted from the X-ray tube 10 is stopped down by the field stop apparatus 11, and then emitted from the top portion of the bed housing 7 so as to pass through the subject. After passing through the subject, the X-ray is received by the spot shot photographing apparatus 4 and converted into the electric signal there.

Figure 2:
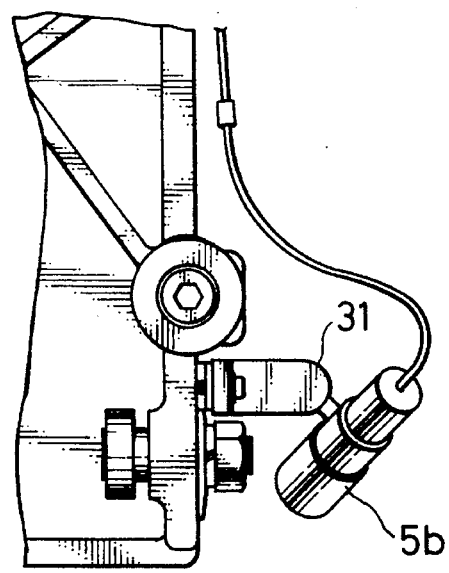
FIG. 2 is a plan view showing one front end portion of a spot carriage top plate viewed from the upper side thereof.
Figure 3:
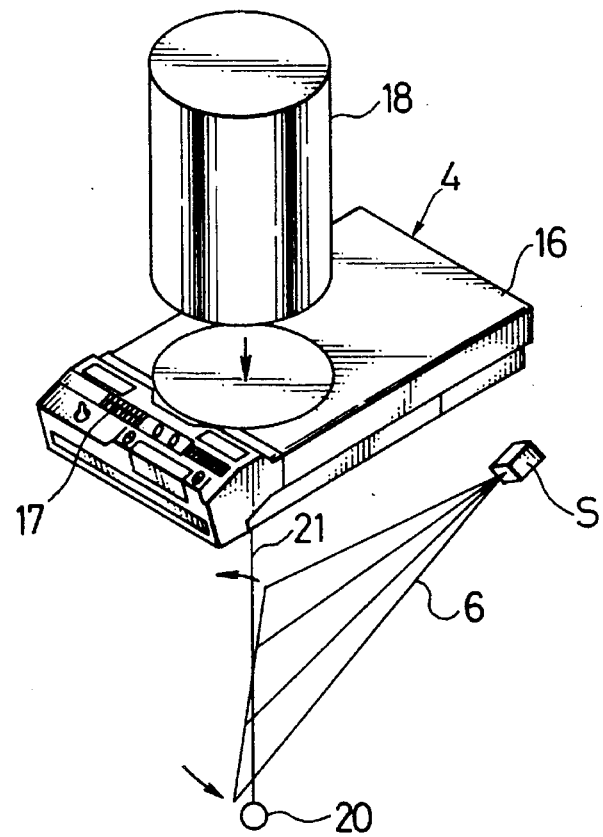
FIG. 3 is a perspective view showing an example of a method of adjusting light projectors in the fluoroscopic photographing table shown in FIG. 1.

FIG. 2 is a plan view showing one front end portion of the spot carriage top plate 15 viewed from the upper side thereof. The light projectors 5a, 5b are arranged respectively at two front ends of the spot carriage top plate 15 constituting part of the spot carriage apparatus 3 so as to be moved tiltably backward/forward and right/left and rotatably by means of universal Joints 31. At this time, the light projector 5a emits plane light 6a spread like a folding fan in the obliquely forward direction to draw a straight line on the subject which is placed on the top plate 12 of the bed apparatus 2, while the light projector 5b similarly emits plane light 6b spread like a folding fan in the obliquely forward direction to draw another straight line on the subject which is placed on the top plate 12 of the bed apparatus 2. As a result, a center of an irradiation visual field of the X-ray emitted from the X-ray tube 10 can be indicated by an intersecting point of these two straight lines.

At this time, these light projectors 5a, 5b are positioned on the outside of the visual field of the I.I 18 constituting part of the spot shot photographing apparatus 4. Therefore, these light projectors 5a, 5b never interrupts an X-ray diagnosis of the subject by the spot shot photographing apparatus 4. However, it is preferable that the light projectors 5a, 5b should be positioned at a location near the center line of the irradiation visual field as much as possible. In the embodiment described herein, a distance between the center line and the light projectors 5a, 5b is set to be about 470 mm.

A method of adjusting these light projectors 5a, 5b will be explained with reference to a perspective view of FIG. 8.

First, a thread 21 to one end of which a weight 20 is connected is prepared. Under the condition wherein the bed apparatus 2 is positioned horizontally, the other end of the thread 21 is connected to a center of the I.I 18 constituting part of the spot shot photographing apparatus 4. The center line of the X-ray irradiation visual field can be found by this thread 21.

In this state, the plane light 6 spread like a folding fan is emitted by one light projector 5a of these light projectors 5a, 5b. Then the light projector 5a is tilted back/forth and right/left and is rotated such that a shade of the thread 21 is projected by this light 6 over the entire surface. Thus, the center line of the X-ray irradiation visual field is adjusted to be included in a flat surface formed by optical paths of the light 6 emitted by the light projector 5a.

In addition, the other light projector 5b is adjusted in the same way as described advance. The light projector 5b is also tilted back/forth and right/left and is rotated. Thus, the center line of the X-ray irradiation visual field is adjusted to be included in a flat surface formed by optical paths of the light 6 emitted by the light projector 5b.

Then, according to the above adjustment, even when the subject is placed on the top plate 12 of the bed apparatus 2 or when the spot shot photographing apparatus 4 is moved in the up/down direction, the center of the X-ray irradiation visual field can be indicated by an intersecting point of the light 6 emitted by these light projectors 5a, 5b.

As has been described above, in this embodiment, these light projectors 5a, 5b are positioned on the outside of the visual field of the spot shot photographing apparatus 4, and the center of the irradiation visual field of the X-ray emitted by the X-ray tube 10 in the bed apparatus 2 can be indicated by the intersecting point of the light emitted by these light projectors 5a, 5b. Therefore, even if the intervening body exists between the field stop apparatus and the subject as in the under type diagnosis apparatus, information such as the center of the irradiation visual field can be displayed. Thereby, since the subject can be positioned with precision, unnecessary X-ray exposure of the subject can be prevented.

Next, an X-ray diagnosis apparatus for a circulatory system as a second embodiment of the present invention will be explained.

Figure 4:
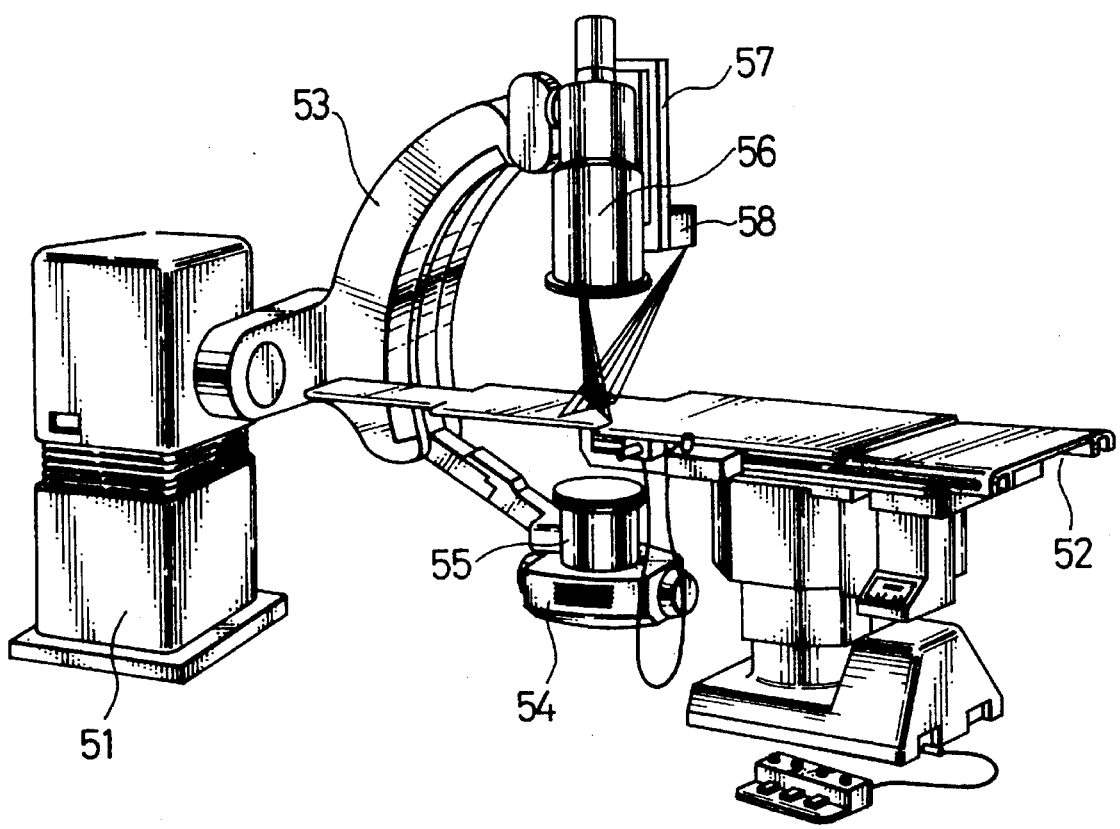
FIG. 4 is a perspective view showing a structure of an X-ray diagnosis apparatus for a circulatory system according to another embodiment of the radiation diagnosis apparatus of the present invention.

FIG. 4 is a perspective view showing a structure of the X-ray diagnosis apparatus used for the circulatory system according to the second embodiment of the present invention.

Here, an X-ray tube 54 and an X-ray field stop apparatus 55 are attached to one end of a C-shaped arm portion 53 supported by a strut section 51. An I.I 56 and an I.I back/forth driving section 57 are attached to the other end of the C-shaped arm portion 53. Before starting the diagnosis, the subject is placed on a catheter table 52 to be put between the X-ray tube 54 and the I.I 56.

In other words, the X-ray emitted by the X-ray tube 54 is stopped down to a desired amount by the X-ray field stop 55 and then passed through the subject placed on the catheter table 52. Then the X-ray passed through the subject is received by the I.I 56 and converted into an electric signal there.

The C-shaped arm portion 53 per se can be moved in the up and down direction by moving an upper portion of the strut section 51 in the up and down direction. The C-shaped arm portion 53 per se can be moved horizontally by using a central axis of the strut section 51 as the rotation center. In addition, when driven by the strut section 51, the C-shaped arm portion 58 can be rotated around the longitudinal direction of the catheter table 52 as the axis of rotation. When the C-shaped arm portion 53 is slid, the X-ray tube 54 and the I.I 56 can be rotated around the lateral direction of the catheter table 52 as the axis of rotation. Furthermore, the I.I 56 can be moved relatively with respect to the C-shaped arm portion 53 in the up and down direction by the operation of the I.I back/forth driving section 57. Moreover, the catheter table 52 per se can move in the up and down direction. By the above various operations, diagnosed parts of the subject can be image-picked up precisely.

In the X-ray diagnosis apparatus for the circulatory system, if, for instance, a light source 58 having two light projectors as in the above first embodiment is provided in the I.I back/forth driving section 57, a center of the irradiation visual field can be indicated. The same adjusting way as that in the first embodiment can be employed in the second embodiment. Note that, in the second embodiment, the light source is not limited to such location, and any place may be used if it is located on the outside of the visual field of the I.I 56. For example, the I.I 56 per se may be installed on the lower side face.

Although, In the above embodiments, the fluoroscopic photographing table and the X-ray diagnosis apparatus for the circulatory system have been explained as preferred embodiments, the present invention is not restricted to such apparatuses and may be applied to other radiation diagnosis apparatuses.

What is claimed is:

1. An X-ray diagnostic table, comprising:

an X-ray generating means positioned beneath a subject placed on a bed, for irradiating X-ray to the subject;

a spot shot photographing device positioned over said subject placed on said bed, and an upper part of which an image intensifier is provided on for picking up said X-ray through said subject as X-ray image;

a first light projecting means provided on said spot shot photographing device side and positioned on an outside of a photographic visual field of said a spot shot photographing device, for emitting first light along a central axis of an irradiation visual field of the X-ray; and a second light projecting means provided on said spot shot photographing device side and positioned on an outside of a photographic visual field of said a spot shot photographing device, for emitting second light intersected with said first light emitted by said first light projecting means along said central axis.

2. An X-ray diagnostic table according to claim 1, further comprising a first adjusting means and a second adjusting means arranged correspondingly to said first light projecting means and said second light projecting means so as to emit light along said center line.

3. An X-ray diagnostic table according to claim 1, further comprising means for driving both said X-ray generating means and said spot shot photographing device in interlock with each other three-dimensionally.

4. An X-ray diagnostic table according to claim 3, wherein said first light projecting means and said second light projecting means are attached to part of said driving means.

5. An X-ray diagnosis table according to claim 4, wherein said part of said driving means is formed of front end portion of a spot carriage top plate constituting part of said driving means.

* * * * *